United States Patent [19]

Czernichow et al.

[11] Patent Number: 4,583,595

[45] Date of Patent: Apr. 22, 1986

[54] METHOD AND APPARATUS FOR OBTAINING FLUID SAMPLES IN A WELL

[75] Inventors: Jean A. Czernichow, Chatenay Malabry; Alain R. Chevassus-More, Fontenay aux Roses, both of France

[73] Assignee: Schlumberger Technology Corp., Houston, Tex.

[21] Appl. No.: 684,422

[22] Filed: Dec. 20, 1984

[30] Foreign Application Priority Data

Dec. 22, 1983 [FR] France .................... 83 20604

[51] Int. Cl.⁴ .............................................. E21B 49/08
[52] U.S. Cl. .................................... 166/264; 175/59; 175/233
[58] Field of Search ............... 166/264; 175/59, 233, 175/234, 235, 236

[56] References Cited

U.S. PATENT DOCUMENTS

| | | | |
|---|---|---|---|
| 3,356,137 | 12/1967 | Raugust | 166/264 |
| 3,358,755 | 12/1967 | Chisholm | 166/264 |
| 4,258,803 | 3/1981 | Thompson et al. | 175/233 |
| 4,463,804 | 8/1984 | Rooney et al. | 166/264 |

FOREIGN PATENT DOCUMENTS

| | | | |
|---|---|---|---|
| 0417614 | 2/1971 | U.S.S.R. | 175/59 |
| 0751981 | 7/1980 | U.S.S.R. | 175/59 |

Primary Examiner—Stephen J. Novosad
Assistant Examiner—William P. Neuder

[57] ABSTRACT

A method and an apparatus for taking a sample representative of the fluid present in a well comprises an elongated body, suitable for being suspended down the well at the end of a cable. The body includes a removable sampling vessel fixed sideways in a recessed portion of the body which vessel is capable of being used, after being filled downhole, as a vessel for transporting the sample under pressure.

16 Claims, 12 Drawing Figures

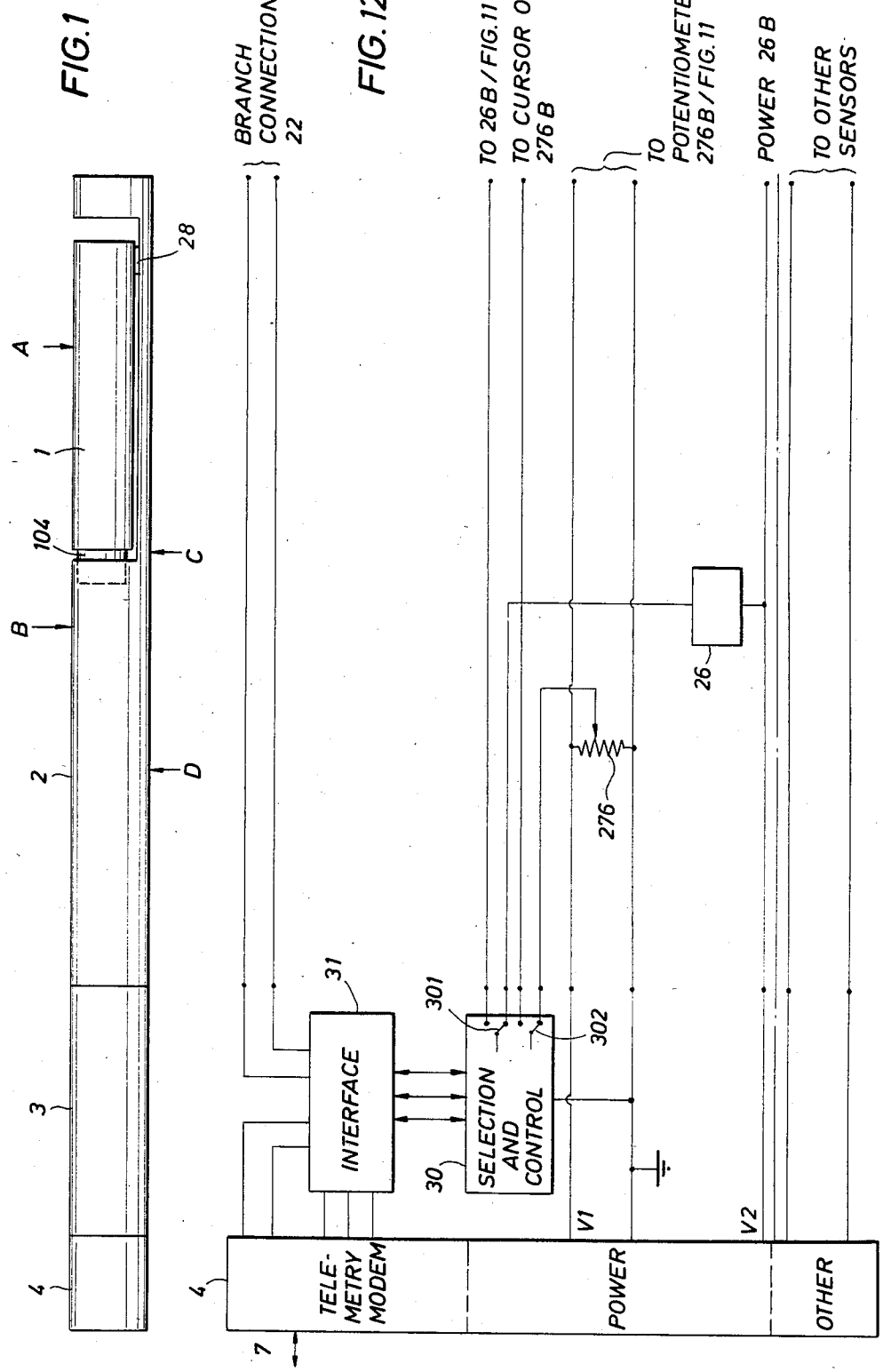

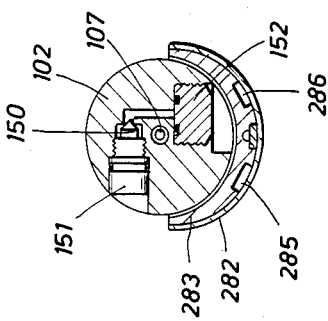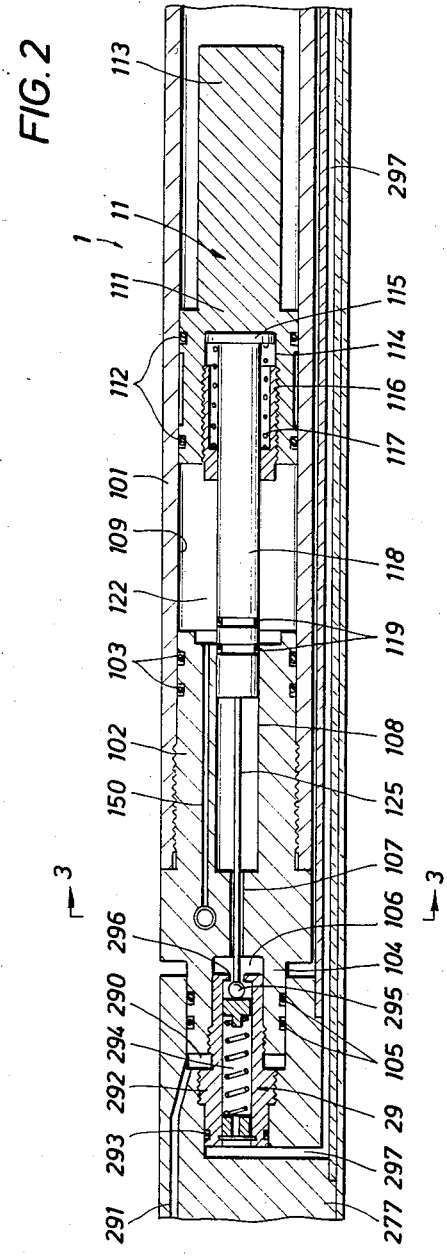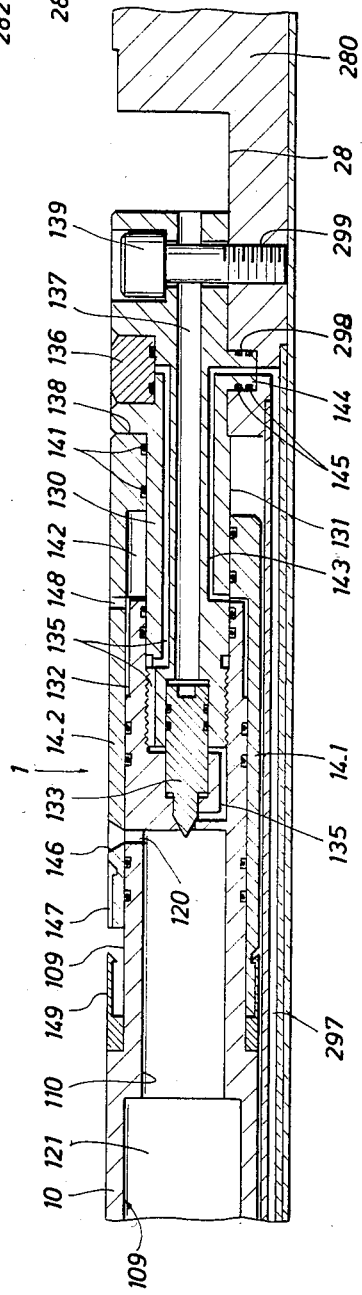

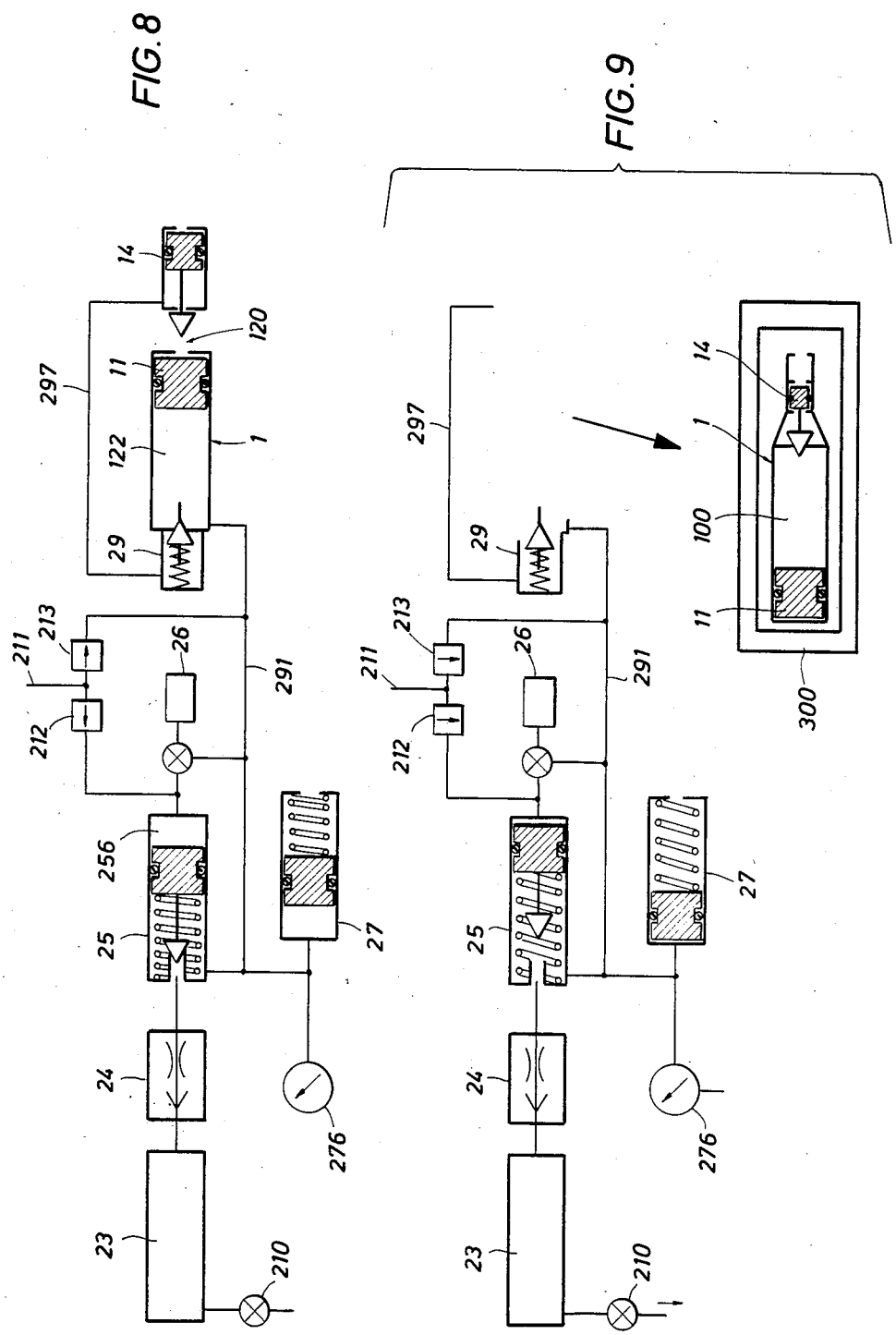

METHOD AND APPARATUS FOR OBTAINING FLUID SAMPLES IN A WELL

BACKGROUND OF THE INVENTION

The present invention relates to methods and apparatus for obtaining samples of fluids present in a well, and more particularly to the obtaining of samples representative of said fluids at a given depth of the well.

The fluids present in a well are generally in the form of a complex mixture of oil, gas and water; in order to study the properties of this mixture at a given depth, it is desirable to take a sample of the fluid under real conditions of volume, pressure, and temperature, and to keep at least one of these dimensions constant until more analysis can be effected. A simple solution is to keep the volume of the sample constant and then to reheat it to the temperature at which the sample was taken.

U.S. Pat. No. 3,095,930 proposes such a solution, which consists in sampling the fluid while allowing a practically zero pressure drop on admission to a sampling vessel. Once the sampling vessel is full, a mechanical control automatically closes the fluid inlet orifice without overcompressing the fluid. The sample, when it has been raised to the surface, is transferred at constant pressure and volume into a transportation vessel for taking it to a laboratory for analysis.

The solution of this prior patent has certain drawbacks. Firstly the transfer operation performed at the surface of the well appears to be dangerous since it is performed at very high pressures which, in particular, require mercury equipment. Further, since only one sample can be taken per descent, and since the sample must be transferred to a transportation vessel on arrival at the surface, a considerable amount of equipment such as the drilling or production tower tends to stand idle for non-negligible lengths of time. Finally, a control rod inside the sampling vessel must be used to close the vessel, which substantially reduces the volume available for the sample.

Fluid samplers have already been described, in particular in the above-mentioned U.S. Pat. No. 3,095,930 and in French Pat. No. 71 02 766 published under the No. 2,123,178. The complex nature of the fluids to be sampled is explained in these documents, as is the polyphase character of their flow. Complete analysis of these fluids can only be performed in a laboratory. It is thus necessary to be able to reproduce in the laboratory the conditions under which the fluid was found when it was sampled.

SUMMARY OF THE INVENTION

To overcome these drawbacks, the proposed method and apparatus for taking a sample representative of the fluid present in a well includes an apparatus of the type comprising an elongate body or housing suitable for being suspended down a well at the end of a cable and comprising a sampling vessel removably fixed to a recess in the housing. The sampling vessel includes a portion delimiting a longitudinal bored cavity provided with an inlet orifice or opening for well fluid, a suction piston, and a closure member for closing said orifice in such a manner as to conserve the taken sample in a fixed volume. Means are provided for controlling the suction piston by applying reduced pressure to its surface which is facing away from the inlet orifice, and second means are provided for controlling the closure member at the end of sampling.

According to a first important characteristic of the invention the longitudinal cavity or bore extends inside a sampling vessel which is removably fixed sideways to a recess in the elongated body in a manner allowing the removal of the vessel from the housing without affecting its contents and is thus capable of serving, once filled and removed, as a transportation vessel for the sample under pressure.

According to another characteristic of the invention, the inlet orifice is placed at one of the ends of the bore and the suction piston slides between a pre-sampling position in which it completely closes the cavity formed between the piston and the one end and its inlet orifice, and an end-of-sampling position in which it stops and in which the closure control means are actuated.

In a preferred embodiment of the invention, the body has a first socket at a first end of said recess in communication with the piston control means; similarly the vessel includes a first annular end portion at its corresponding first end and suitable for insertion into the first socket. At its other end, the recess in the body includes a flat fitted with a second socket in communication with the closure control means; and similarly the vessel includes at its corresponding second end a second annular end portion suitable for insertion in a sealed manner in the second socket, together with fixing means for fixing it to said flat.

According to an additional aspect of the invention, the vessel further includes a second bore extending its cavity away from the inlet orifice, and communicating with the inside of the first end portion. The piston control means is arranged to apply reduced pressure to the inside of the first socket, and in that a stop piston is connected to the suction piston, and is guided to be inserted in a sealed manner in the second bore, thus marking the end of sampling. The closure control means include a stop valve actuated by a rod connected to said stop piston, the valve causing the inside of the first end portion to communicate with the inside of the second socket.

The connection between the suction piston and the stop piston is advantageously made via two-way abutment surfaces permitting relative displacement against a resilient return force after the end of sampling.

According to another aspect of the invention, the closure member for the inlet orifice comprises an annular piston which is axially movable over an outside cylindrical surface of the vessel between a working position in which it presents a similar orifice over the inlet orifice, and a closure position in which the inlet orifice is closed. The annular piston and the vessel delimiting an internal annular volume when the piston is in its working position. The vessel includes a tube in communication with said annular internal volume to control the evacuation thereof and allow the annular piston to be displaced to its second position at the end of sampling.

BRIEF DESCRIPTION OF THE DRAWINGS

Other characteristics and advantages of the invention appear from an examination of the following detailed description and the accompanying drawings, in which:

FIG. 1 is a diagrammatic view of a fluid sampler apparatus in accordance with the invention;

FIG. 2 is a longitudinal section through the portion of FIG. 1 lying between points A and B;

FIG. 3 is a cross section on a section line III of FIG. 2;

FIG. 4 is a longitudinal section through the portion of the FIG. 1 sampler to the right of point A;

FIGS. 8 and 9 are diagrams showing the operation of a sampler in accordance with the invention;

FIG. 12 is an electronic block diagram of the sampler in accordance with the invention.

DESCRIPTION OF THE PREFERRED EMBODIMENT

Figure 5:
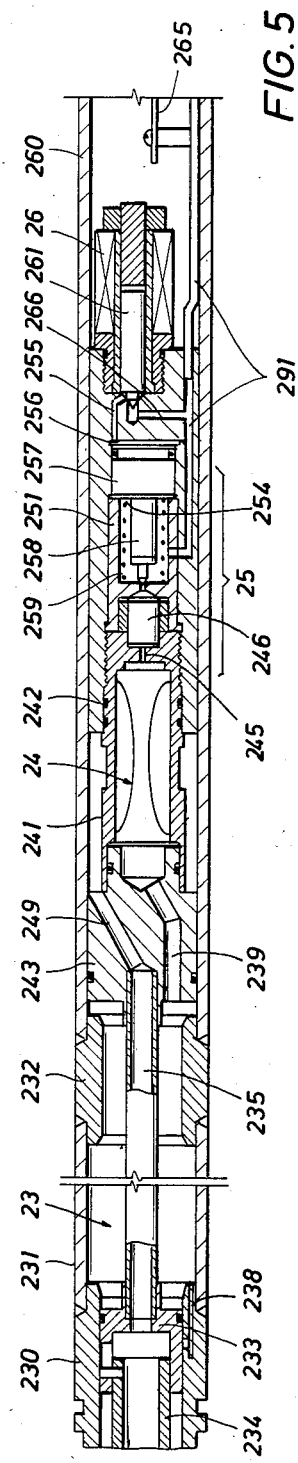
FIG. 5 is a longitudinal section corresponding substantially to the portion of the FIG. 1 sampler to the left rof point B.

A string of tools including one or more samplers in accordance with the invention is disposed in known manner at the end of a cable (not shown). The various tools may be interconnected by a standard 22-pin connection system.

FIG. 1 shows the general structure of a sampler in accordance with the invention. It compries an elongate body or housing suitable for being suspended down a well at the end of a cable. In FIG. 1 this body is supposed to be made of two portions 2 and 3 which are interconnected by a 22-pin connection. At the right hand end of the Figure (the bottom end in a well), the portion 2 of the body includes a recess into which a sampling vessel 1 is removably fixed sideways. The vessel has an end portion 104 which is axially engaged in the body 2. It is fixed sideways to a flat indicated diagrammatically at 28 in FIG. 2.

In this structure, the portion 3 includes an add-on electronic unit for the sampler, which unit is described below.

The the left of point D, the portion 2 includes an air reservoir 23 followed by a restriction 24, a hydraulically controlled valve 25, and an electrically controlled valve 26. These items appear in the diagram of FIG. 8. They are described in greater detail below.

To the right of point D, and up to point C, the portion 2 comprises an equalizing reservoir 27 to which a manometer 276 is connected.

This assembly of items is associated with a first main tube 291 which extends as far as the sampling vessel 1. A piston 11 is housed in the sampling vessel, said piston being movable between a pre-sampling position in which it completely closes the inlet orifice 120 to the cavity 12 of the sampling vessel 1, and an end-of-sampling position where it stops. At that moment, in a manner which is described below, a stop valve 29 is operated to put the first main tube 291 into communication with a second main tube 297. This tube employs another piston system 14 which closes the inlet orifice 120.

The sampling vessel can then be separated from the sampler, and placed in a transportation safety container 4 as shown in FIG. 9.

Reference is now made to FIGS. 2 to 4 which show the portion of the body around the sampling vessel in greater detail.

Materially the sampling vessel 1 is principally constituted by a generally cylindrical sleeve 101 which is closed at both ends. Its left hand end is closed by an end piece 102 screwed into the sleeve and provided with a pair of sealing rings 103. The inside wall of the sleeve 101 defines a cylindrical surface 109a in which the suction piston 11 slides. More precisely, the piston 11 comprises a guide portion having a cylindrical outer surface that co-operates with the surface 109a via a pair of sealing rings 112.

At its right hand end, the suction piston 11 comprises an axial cylindrical projection 113 suitable for being exactly received in a second axial bore 110 which follows the bore 109, is of smaller diameter, and is coaxial therewith.

The cavity usable for sampling is thus defined by the bore 110, and by the portion of the bore 109 which is situated to the right of the piston 11. At the extreme right hand end of the cavity, and inlet orifice 120 passes through the sleeve 101. The sleeve 101 is closed radially to close the sampling vessel thus formed, and referenced 121. However, the end portion of the sleeve 101 houses various items of additional equipment which are described below.

To the left of the piston 11 there is another portion 122 of the internal cavity of the sampling vessel 1. The adjacent end piece 102 has a central bore 108 in which a stop piston 118 having a pair of sealing rings 119 may be received.

The suction piston 11 is accurately guided in the bore 109. It in turn comes to provide accurate guidance for the stop piston 118 to enable it to be inserted exactly into the bore 108. To this end, the stop piston 118 has an end shoulder 115 which is normally urged by a spring 117 to press against the right hand end of a cavity 114 made in the portion 111 of the suction piston 11. The spring 117 is further held in place by a thimble 116 screwed into the portion 111 of the piston 11, with the right hand end of the thimble 116 forming a second stop for the shoulder 115.

To the left of its bore 108, the end piece 102 has a passage 107 which opens out to the inside 106 of an annular end portion 104 which is fitted with a pair of sealing rings 105. To its left, the stop piston 118 is extended by a thin rod 125 which is coaxial therewith and which is an easy fit into the passage 107.

While the piston 11 is far enough to the right for the first sealing ring 119 to be not yet engaged in the bore 108, the left hand face of the piston 11 is subjected to the action of a fluid filling the cavity 122 and extending up to the inside 104 of the end portion 104.

The end portion 104 and its a pair of sealing rings 105 enter a socket 290 in the body 2. The first main tube 291 also terminates in the socket 290. The fluid pressure existing in the tube 291 can thus be used to control the movement of the suction piston 11 from its position (not shown) to the far right of the cavity 121 up to its end of sampling stop position (as shown).

A stop valve with an overall designation 29 is also screwed into the socket 290. The valve has a body 292 which is threaded with a peripheral sealing ring 293 into the body 2 of the sampler in accordance with the invention. Inside, the valve 29 includes resilient return equipment 294 for urging a ball 295 against the valve seat 296.

When the pistons 11 and 118 are in the position shown in FIG. 2, ie. the stop position at the end of sampling, the sealing rings 119 prevent fluid from flowing from the vessel 122 towards the tube 291. However, pressure remains applied to the right hand face of the piston 118 which continues its movement a short distance against the resilient return force 117. Its rod 125 then pushes the ball 295, thus enabling fluid pressure to pass through the equipment 294 to the tube 297 beginning at the left of the stop valve 29. The tube 297 goes through to the bottom of the part 277 of the body 2 to pass the entire length of the figure to the right in another part 280 likewise of the body 2.

The part 280 contributes to defining the recess in which the sampling vessel 1 is housed: to this end it includes a flat 28 in which there is a second socket 298. There is also a threaded bore 299, with the socket 298 and the bore 299 being radially directed, while the above-mentioned socket 290 is axial.

The tube 297 (the second main tube) opens out into the socket 298. A second end portion 144 of the sampling vessel 1 is received in the socket 298, together with a pair of sealing rings 145. The end portion 144 is a part of the end piece 130 of the sampling vessel 1. The end piece 130 is screwed into the right hand end of the sleeve 101. On its outside, the right hand end of the sleeve 101 defines a cylindrical surface 109a having two pairs of sealing rings on either side of the inlet orifice 120. An annular piston 14 slides over the outside surface 109a. Its right hand end is provided with an inwardly directed tubular shoulder which has a bore fitted with a pair of sealing rings 141 sliding over the outside surface 131 of the part 130.

The annular piston is movable between a closure position 14-1 shown in the bottom half of FIG. 4 and a sampling position 14-2 shown in the top half of FIG. 4. In the sampling position its right hand end abuts against the should 138 of the part 130. An orifice 146 through the annular piston 14 then comes opposite the inlet orifice 120 of the sampling vessel 1. A cavity 142 is defined between the inside of the annular piston 14 and the outside surface 131.

The cavity 142 communicates with a tube 143 which opens out inside the end portion 144 opposite to the second main tube 297. Thus, reduced fluid pressure applied to the tube 297 will draw the piston 14 to the left.

The piston 14 includes a guide peg 148 sliding in a groove in the sleeve 101 up to the stop 132.

The annular piston is then in the closure position 14-1 in which it is held by a set of hooks such as 149 which are regularly spaced around its periphery and; which engage a catch 147 in the left hand end of the annular piston 14.

The right hand end of the sleeve 101 houses another valve 133 which is used for draining the fluid in the laboratory. This valve opens through the wall of the cavity 121. It is operable via a cylindrical bore 137, eg. by means of a screwdriver. When the valve 133 is opened it causes the interior of the cavity 121 to communicate with a tube 135 which ends behind a drain plug 136.

Finally, a screw 139 engages the threaded bore 299 for releasably fixing the sampling vessel 1 to the body of the sampler in accordance with the invention.

Reference is now made to FIG. 3 which is a cross section of FIG. 2 through its end piece 102. It can be seen that the end piece has another tube 150 which communicates with a cavity 122 situated to the left of the suction piston 11. The tube 150 can be seen in FIG. 3 where it appears that it ends in a working vessel of a mechanically controlled valve 151. This valve enables the tube 150 to communicate with an outlet via a drain plug 152. This arrangement is useful for determining the bubble point of the sample, on site, and after the tool has been returned to the surface.

It can also be seen in FIG. 3 that at this section the body is constituted by two half-shells 282 and 283 which are welded together. Passages 285 and 286 are provided between the half-shells, in particular for passing electrical conductors leading to downstream tools.

Figure 6:
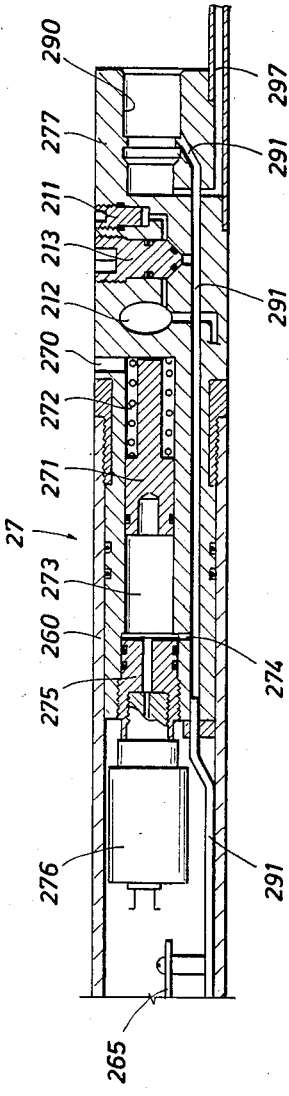
FIG. 6 is a longitudinal section through the portion of the FIG. 1 sampler lying between points D and C.
Figure 7:
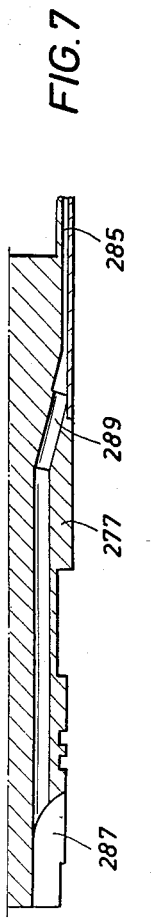
FIG. 7 is a longitudinal section through a fragment of the FIG. 6 sampler, taking in a different section plane.

Reference is now made to FIGS. 5 to 7. These figures show the entire first control means for determining movement of the suction piston 11. The second control means, essentially constituted by the stop valve 29, switch over the action of the first control means to the annular closure piston 14.

An air vessel 23 is defined to the left of FIG. 5. One end of an annular sleeve 231 is fixed to an end piece 230 and the other end is fixed to a ring 232 which is fixed in turn to along cylindrical sleeve 260.

To the left of the air vessel 23, the end piece 230 houses an annular support 233 which forms a bearing surface for a hollow rod 235. The rod 235 has its other end resting on a second ring 243. The rings 233 and 243 together with the walls 230 to 232 and the left hand end of the sleeve 260 externally delimit the air vessel. The air vessel 23 is put at atmospheric pressure on the surface, or at a pressure close thereto. At depth, its exterior is subjected to the hydrostatic pressure in the well. Its inside pressure, while increasing with temperature, will nonetheless remain well below the well pressure.

To the left of the ring 233, there is a tube 234 which serves as a support for a 22-pin electrical connection. The interior of the vessel 23 communicates via a tube 238 with a valve (not shown in FIG. 5, but referenced 210 in FIGS. 8 and 9) which serves, on the surface, for putting the air vessel 23 at atmospheric pressure.

A reduced diameter axial extension of the part 243 supports a cylindrical part 241 having a restriction 24. At the right hand end of the part 241 is closed except for a narrow orifice 245 which contributes to defining the restriction 24. The downstream end of the restriction 24 communicates with the air vessel 23 via a tube 239 running through the part 243.

Upstream from the restriction 24 there is a hydraulically controlled valve. Immediately after the orifice 245, the part 241 defines a cavity 246 which is surrounded by an outwardly directed annular thread. The seat 251 of the hydraulically controlled valve is placed on the thread. The part 241 and the seat 251 are held together by an annular part 242. The inside of the valve seat 251 defines a cavity 259. Further to the right, the part 242 defines a bore for a piston 257 which constitutes the control unit for moving the needle 258 of the valve 25. The needle 258 moves against the resilient return force of a spring 254 in the cavity 259 in such a manner that its sharp point closes the orifice for communication between the cavity 246 and the cavity 259. The right hand face of the piston 257 is subjected to the pressure reigning in a cavity 256 which constitutes a control vessel for the valve 25. The cavity 256 is subjected to the pressure reigning in the tube 255.

Further right, the end of the part 242 has an inwardy directed thread which receives an electrically controlled valve having a general reference 26. The electrically controlled valve 26 is located in a housing inside the cylinder 260, which housing also contains a printed circuit 265, and a manometer 276 which is described below with reference to FIG. 6.

Electrical conductors reach the printed circuit via the hollow rod 235, the passage 249 which extends it through the part 243, the annular empty space surrounding the left hand end of the part 241, and passages (not shown) through the part 242. Two of these electrical conductors supply DC to the winding of the electrically controlled valve 26. When the DC is of the appropriate polarity, the valve core 261 is moved to the right, thereby opening a fluid passage between the tube 255 and a tube 266.

The first main tube 291 communicates both with the cavity 259 of the hydraulically controlled valve, and with the tube 266. The tube 291 passes through the housing in the cylinder 260 to join (see FIG. 6) the tube 291 inside the part 277 which extends to the recess in which the sampling vessel 1 is received.

The left hand end of the part 277 has a bored out cavity 273. One of the ends of the bored out cavity communicates via an orifice 270 to the surroundings, i.e. to the muds met at depth in a production tube. A piston 271 fitted with sealing means slides in the cavity 273 with a resilient return spring 272 being fitted between the piston and the right hand end of the cavity 273. At its other end, the cavity 273 is closed by a threaded end fitting 275 through which there passes a passage leading to the above-mentioned manometer 276. This manometer detects the pressure reigning at depth and may, for example, be a potentiometer type pressure transducer. The electrical signal that it supplies is received by the printed circuit 265 and returned to the surface.

A short tube 274 puts that part of the cavity 273 which is to the left of the piston 271 into communication with the first main tube 291. The assembly just described thus constitutes a pressure equalizing vessel 27 for bringing the pressure inside the tube 291 close to the surrounding pressure at sampling depth.

Further to the right, FIG. 6 shows two valves 212 and 213 which are separately connected to the inlet orifice having a plug 211. The valve 212 (not shown in detail) serves to direct hydraulic fluid to the control vessel 256 via a tube which is now shown in FIG. 5 (see FIG. 8). The valve 213 serves to fill the sonde by means of the tube 291 which feeds all the vessels which are connected thereto.

Finally, to the far right of FIG. 6 there can be seen the socket 290 for receiving the end portion 104 of the sampling vessel and the connection of the tube 291 with said socket 290.

Although the second main tube 297 is located in a different section plane, it is also shown here running from the bottom of the socket 290. Naturally, the tubes 291 and 297 are not in communication where they cross.

FIG. 7 shows another view taken in a different section plane. It shows how the electrical connections from the inside of the cylinder 260 can pass via 287 into a tube 289 to reach one of the passages such as 285 or 286 provided downstream.

Figure 11:
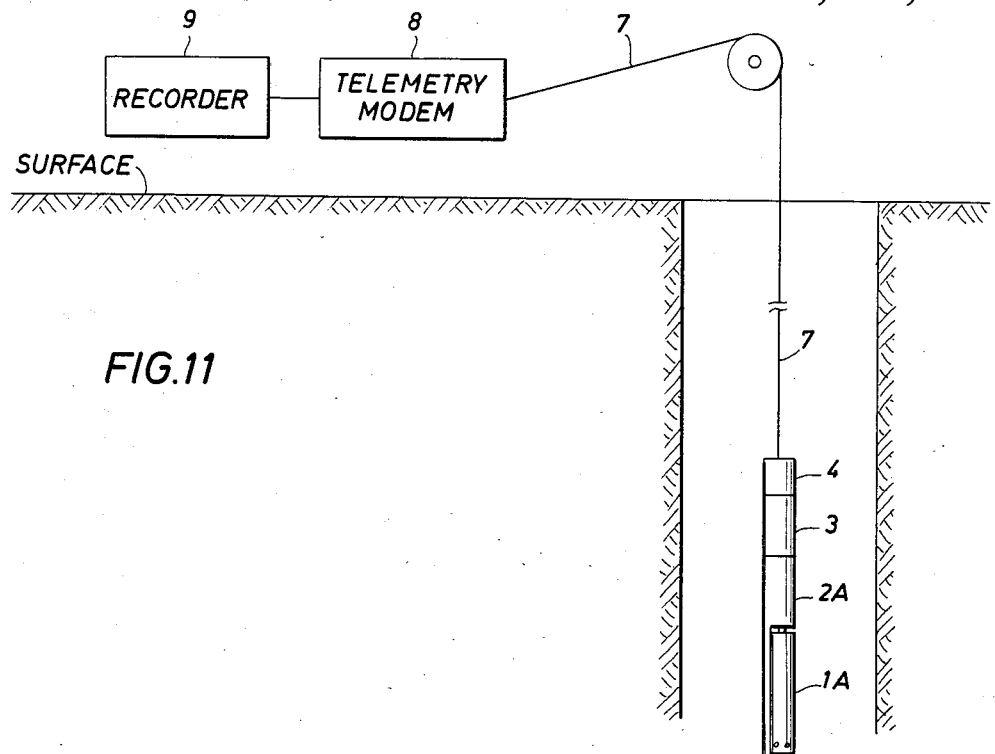
FIG. 11 shows different tool assemblies for lowering and using one or more samplers in accordance with the invention.

Reference is now made to FIGS. 1 and 11 to 12.

The portion 3 of the sampler includes an electronic unit for which FIG. 12 is a block diagram. The unit comprises an interface 31 connected firstly to a two-way multiplex transmission unit 4 which is itself connected to a cable 7, and secondly via a 22-pin connection to a circuit 30 for selecting and controlling the electrically-controlled valve 26 and the manometer 276.

The unit 4 contains a modem which is not shown in detail for exchanging digital data over the cable 7 with a surface modem 8. The digital transmission system thus enables instructions to be sent down from the surface to the selection and control circuit, and also enables readings made by the manometer 276 to be transmitted up to a surface recorder 9.

The electronic unit 3 performs the same functions for a possible second sampler 1B and 2B as shown in FIG. 11, and equipped with a manometer 276B and an electrically controlled valve 26B.

The interface 31 digitizes the readings from the manometer 276 and prepares them for application to the modem.

The selection and control circuit 30 is controlled from the surface and serves to switch, 301, select and activative one or other electrically operated valve, eg. depending on the polarity of the control current.

The manometer 276 may be a potentiometer type transducer supplied with a DC voltage V1. The electrically operated valve 26 is actuated by a DC voltage V2. It should be observed that not all of the 22 pins are used, so other measuring devices 5 and 6 such as temperature, density, and flow rate detectors may be added.

The operation of the sampler in accordance with the invention is now described:

At the surface, the valve 210 (FIGS. 8 and 9) is used to put the air vessel 23 at atmospheric pressure.

The valve 212 (FIG. 8) is opened to bring the control vessel 256 of the hydraulically controlled valve 25 to high pressure, eg. to 15 bars, by means of the fluid inlet 211.

The valve 212 is then closed and the valve 213 is opened. The same fluid inlet 211 then enables the first main tube 291 to be raised to a slightly lower high pressure, eg. 10 bars (if the valve 25 were differently constructed, higher pressure could be used in the tube 291). Since the piston 14 is in its open position, the suction piston 11 is pushed home to completely close the cavity 121, as shown diagrammatically in FIG. 8. A pressure of 10 bars then reigns in the cavity 122. The same is true of the second main tube 297, the sampling vessel naturally being in place. Finally, the same pressure of 10 bars reigns inside the working vessel 259 of the hydraulically controlled valve 25 and inside the cavity 273 of the pressure equalizing vessel 27.

Figure 10:
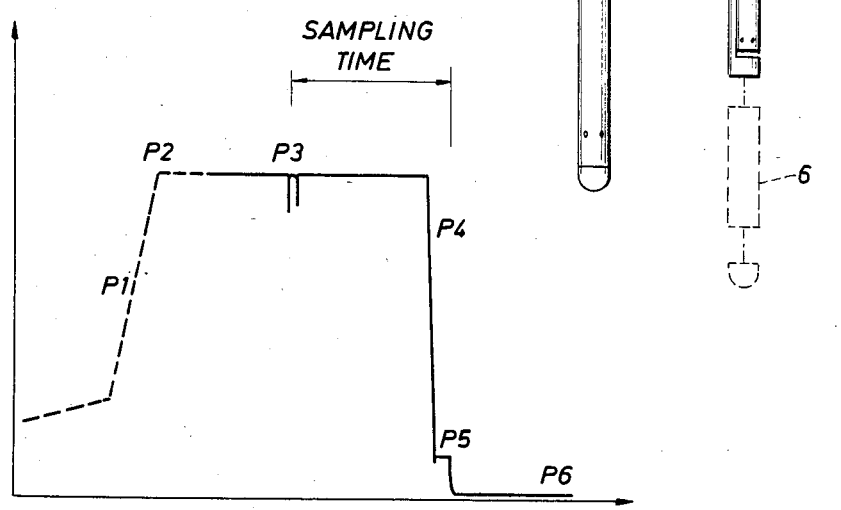
FIG. 10 is a graph of pressure, which also illustrates the operation of the sampler in accordance with the invention.

The sampler is now ready for sampling and is lowered to depth. As it goes down, the surrounding pressure is monitored by means of the manometer 276. A typical pressure curve is shown in FIG. 10. The portion P1 corresponds to the pressure in the well. The bend in the portion P1 corresponds the so-called "bubble point" pressure.

On reading the desired depth for sampling, DC of appropriate polarity is applied to the electrically controlled valve 26. At this depth, the pressure in the well is high. The presence of the compensation vessel 27 makes it possible to speak in terms of relative pressures (relative to the well pressure). The valve 26 then puts the control vessel 256 of the hydraulically controlled valve 25 in communication with the first main tube. The vessel was at 15 bars relative, while the first main tube was at 10 bars relative. The pressures then equalize to 10 bars relative since the volume of the control vessel 256 is small compared with the rest of the volume of the control liquid. The piston 257 of the hydraulically controlled valve 25 moves to the right, putting the downstream end of the restriction 24 in communication with the first main tube 291. The fluid then moves slowly through the restriction 24 towards the air vessel 23. Since the stop valve 29 is closed, this movement of fluid reduces the pressure on the left face of the suction piston 11, thereby causing it to move to the left and thus starting sampling. In FIG. 10, the portion P2 marks the pressure reaching the pressure corresponding to the desired depth, and it is separated from the portion P3 which corresponds to the sampling period per se by an artefact due to the actuation of the electrically controlled valve.

The suction piston 11 moves to the left. At the moment that the rod 125 actuates the ball 295 of the stop valve, the reduced pressure inside the first main tube 291 is transmitted to the second main tube 297. The annular piston 14 moves to the left, closing the suction orifice 120 and latches onto the hooks 149. At the same time, the first of the sealing rings 119 comes into contact with an inlet cone to the bore 108, thereby isolating the cavity 122 from the pressure of the sample. As soon as the cavity 120 is closed, a pressure drop occurs on the left face of the piston 118 which thus continues to move to the left until it abuts against the part 116 (with the suction piston 11 stationary) thereby firmly engaging the sealing rings 119 and completely sealing off the vessel 122.

The person skilled in the art will understand that the sample obtained is thus kept at constant volume.

During this step of closing the sampling vessel, the pressure drops along a vertical line P4. It will then continue to drop following a curve P5 until it equalizes with the pressure in the air vessel.

After these operations, the string of tools lowered down the well may be raised, if only one sample was to be taken. However, the invention also enables a plurality of samples to be taken. FIG. 11 shows a first sampler 1a, 2a, 3a which may be followed by another sampler 1b, 2b or by another tool outlined at 5. The second sampler could also be followed by another tool 6. All these tools are interconnected by 22-pin connections as already mentioned.

In such a case, the string of tools is removed only after the other tools have also been used.

One particular point should be noted when a second sampler is provided downstream from the first: as mentioned above, the electrically controlled valve 26 responds to DC of a determined polarity. The second sampler may be of identical structure, and yet be selectively controlled simply using the opposite polarity to open the electrically controlled valve. Naturally a variant would consist in controlling a plurality of electrically operated valves via separate and/or multiplexed links, which would make it possible to cascade more than two samplers in accordance with the invention.

After the, or each, sampling operation is over the string of tools lowered down the well is raised to the surface.

Unlike prior art samplers, there is no need for decanting. The retaining screw 139 of the, or each, sampling vessel is simply undone, and the vessel(s) removed from the lowering tool. The vessel can then be transferred to a laboratory inside a safety container (300) as shown in FIG. 9.

It is frequently desirable to be able to ensure on site that samples which have just been taken are valid. One of the current means of doing this is to measure the "bubble point" pressure of the samples. This is done by determining the repressurization curve of the sampled fluid.

In a sampler in accordance with the invention, it appears that a volume of fluid remains in the cavity 122 of the sampling vessel 1. This volume of control fluid, generally oil, can be used to verify the bubble point pressure without running the risk of losing the sample. Further, tapping off a known quantity of fluid from the cavity 122 makes it possible to expand the sample partially by creating a pocket of gas and to absorb oil expansion due to temperature changes during transport. Naturally, for laboratory analysis, the same known quantity of fluid is re-injected into the cavity 122. The sample is thus returned to its initial volume before being drawn off via the valve 133 and the orifice 136.

To determine the bubble point, the following steps are performed:

A suitable vessel is connected to the tube 150 after the plug 152 has been removed. By operating the valve 151, fixed quantities of liquid are removed in from the cavity 122, eg. quantities of two cubic centimeters each, while the pressure is being measured. The pressure measurement readily indicates when gases dissolved in the sample are liberated. Naturally, the same operation may be performed on the various sampling vessels used in a single investigation at depth.

In conclusion, it appears that the present invention offers the following advantages:

The beginning of sampling is obtained by means of an electrically controlled valve which is actuated from the surface, by a conducting link or by telemetry; this means that an explosive actuator as used in the prior art is unnecessary.

All the hydraulic lines and tubes are compensated.

The sampling speed is adjustable by suitably adjusting the restriction 24. It appears that the restriction can be adjusted in such a manner as to obtain constant sampling time, typically two minutes, regardless of the sampling pressure. This provides operational control over the sampling operations per se.

The sampling vessel itself is removable and is used as means for transportation to the laboratory.

The bubble point can be checked.

The sampling vessel is very efficiently closed, so no operations involving mercury are required.

The sampler is easily connected in series with other types of sonde, and in particular with a second sampler.

What is claimed is:

1. A borehole apparatus for obtaining a respresentative fluid sample in a borehole comprising:
 a housing adapted for passage through a borehole;
 a sampling vessel removably fixed to a recess in said housing, said vessel having a cylindrical bore and a sample admitting opening;
 a piston sealingly positioned in said bore and relatively movable between a collapsed position of adjacency and an extended, space-apart position relative to one end of said bore to define therebetween a fluid sample-receiving chamber;
 actuable means, in communication with said bore, for controlling the relative movement of said piston in said chamber, said actuable means being provided in said housing;
 means for closing said opening after a given relative movement of said piston is effected in response to the actuation of said controlling means; and means for severing the communication between said controlling means and said chamber after the closing of said opening for allowing the removal of said vessel from said housing without affecting said vessel or its contents by the act of removal.

2. An apparatus according to claim 1, wherein said opening is placed at one of the ends of the bore and in that said piston slides between the collapsed position in which it completely closes the opening, and a given extended position at which it stops its relative movement and at which said closing means effects the closing of said opening.

3. An apparatus according to claim 1, wherein said housing is provided with a first socket at a first end of said recess adapted to receive therein one end of said vessel and to establilsh therethrough communication between said actuable means and said bore.

4. An apparatus according to claim 3, wherein the other end of the recess includes a flat fitted with a second socket adapted to receive therein a nozzle which is provided on said vessel and to establish therethrough communication between said closing means and said actuable means.

5. An apparatus according to claim 4 wherein said actuable means comprise:
- a tube communicating with the inside of the first socket;
- an air vessel initially set to atmospheric pressure at the surface;
- a restriction having one end connected to the air vessel;
- a hydraulically operated valve having a control vessel and a working vessel which can be connected on command to the other end of said restriction, said working vessel being further connected to the tube;
- an electrically controlled valve suitable for being actuated from the surface, said electrically controlled valve being suitable for establishing interconnection between the hydraulically controlled valve's control vessel and the tube;
- an equalizing vessel containing a compensation piston having one face connected to said tube and having its other face subjected to a resilient return force at the same time as the surround pressure at depth; and
- means suitable for being operable in the presence of the sampling vessel on the sampler to put the control vessel of the hydraulically controlled valve at a first high pressure, and then to put the tube at a second high pressure such that while the sampling orifice is open, the sampling piston is brought into its pre-sampling position in which it fully occupies the sampling cavity and closes the inlet orifice, and the operation of the electrically controlled valve at depth causes a sample to be taken.

6. An apparatus according to claim 5, further comprising:
- a pressure sensor-transducer is connected to the said tube, thereby enabling pressure data to be electrically transmitted to the surface, for monitoring the operations of lowering to depth and sampling.

7. An apparatus according to claim 4, wherein said vessel further includes a second bore communicating with said one end of said vessel; a second piston, slideably engaged in a sealing manner in said second bore and is connected to the first piston; and wherein said closing means includes a stop valve actuated by a rod connected to said second piston, said valve causing the inside of said one end of said vessel to communicate with the second socket.

8. An apparatus according to claim 7, wherein the connection between the first piston and the second piston is made via two-way abutment surfaces permitting relative displacement against a resilient return force after the end of the relative movement of said first piston.

9. An apparatus according to claim 1, wherein said closing means comprises an annular piston which is axially movable over a cylindrical cavity of said housing between a first position in which said opening is unobstructed, and a closure position in which said opening is closed, said annular piston being subject to relative motion in response to the establishment of communication between said cylindrical cavity and said bore.

10. An apparatus according to claim 9, further comprising means for locking the annular piston in its closure position subsequent to the closing of said opening.

11. An apparatus according to claim 1 wherein at the end of the given relative movement of the piston its position is intermediate in the bore, the apparatus further comprising means for enabling communications between the residual volume in said bore adjacent to the piston on its side not adjacent to the opening and a drain plug to enable on site bubble point verification of the sample.

12. A borehole apparatus for obtaining a representative fluid sample in a borehole comprising:
- a housing adapted for passage through a borehole;
- a sampling vessel removably fixed to a recess in said housing, said vessel having a cylindrical bore and a sample admitting opening;
- a piston sealingly positioned in said bore and relatively movable between a collapsed position of adjacency and an extended, space-apart position relative to one end of said bore to define therebetween a fluid sample-receiving chamber;
- actuable means, in communication with said bore, for controlling the relative movement of said piston in said chamber, said actuable means being provided in said housing;
- means for closing said opening after a given relative movement of said piston is effected in response to the actuation of said controlling means; and
- means for severing the communication between said controlling means and said vessel after the closing of said opening for allowing the removal of said vessel from said housing without affecting said vessel or its contents by the act of removal;
- wherein said closing means comprises an annular piston which is axially movable over a cylindrical cavity of said vessel between a first position in which said opening is unobsructed, and a closure position in which said opening is closed, said annular piston being subject to relative motion in response to the establishment of communication between said cylindrical cavity and said bore.

13. An apparatus according to claim 12, further comprising means for locking the annular piston in its closure position subsequent to the closing of said opening.

14. An apparatus according to claim 12 wherein at the end of the given relative movement of the piston its position is intermediate in the bore, the apparatus further comprising means for enabling communications between the residual volume in said bore adjacent to the piston on its side not adjacent to the opening and a drain plug to enable on site bubble point verification of the sample.

15. A method for obtaining a representative fluid sample in a borehole comprising the steps of:

lowering a housing adapted for passage through a borehole into a borehole;

removably fixing a sampling vessel to a recess in said housing, said vessel having a cylindrical bore, a sample admitting opening and a piston sealingly positioned in said bore and relatively movable between a collapsed position of adjacency and an extended, space-apart position relative to one end of said bore to define therebetween a fluid sample-receiving chamber;

controlling the relative movement of said piston in said chamber through actuable means provided in said housing;

admitting a sample of borehole fluid into the bore;

closing said opening after a given relative movement of said piston is effected; and severing the communication between said housing and said vessel after the closing of said opening for allowing the removal of said vessel from said housing without affecting said vessel or its contents by the act of removal.

16. The method of claim 15 wherein the end of the given relative movement of the piston its position is inermediate in the bore, the method further comprising the step of enabling communications between the residual volume in said bore adjacent to the piston on its side not adjacent to the opening and a drain plug to enable on site bubble point verification of the sample.

* * * * *